(12) United States Patent
Kim et al.

(10) Patent No.: US 10,371,709 B2
(45) Date of Patent: Aug. 6, 2019

(54) CIRCULAR TYPE CARTRIDGE ENABLING CENTRIFUGATION AND MODULAR AUTOMATIC ANALYZER USING THE SAME

(71) Applicant: I-SENS, INC., Seoul (KR)

(72) Inventors: Kyungho Kim, Seoul (KR); Jae Phil Do, Seoul (KR); Jaewon Jung, Gyeonggi-do (KR); Jung Uk Ha, Daejeon (KR); Sang Taek Shin, Incheon (KR); Seok-Won Lee, Gyeonggi-do (KR); Yungjoon Jin, Seoul (KR); Yusung Kim, Seoul (KR)

(73) Assignee: I-SENS, INC., Seoul (KR)

( * ) Notice: Subject to any disclaimer, the term of this patent is extended or adjusted under 35 U.S.C. 154(b) by 102 days.

(21) Appl. No.: 15/482,467

(22) Filed: Apr. 7, 2017

(65) Prior Publication Data

US 2017/0292967 A1 Oct. 12, 2017

(30) Foreign Application Priority Data

Apr. 8, 2016 (KR) .................. 10-2016-0043177
Mar. 21, 2017 (KR) .................. 10-2017-0035572

(51) Int. Cl.
*G01N 35/02* (2006.01)
*G01N 35/04* (2006.01)
(Continued)

(52) U.S. Cl.
CPC .......... *G01N 35/025* (2013.01); *B01L 3/5021* (2013.01); *B04B 5/0407* (2013.01);
(Continued)

(58) Field of Classification Search
None
See application file for complete search history.

(56) References Cited

U.S. PATENT DOCUMENTS

| 5,149,501 A | 9/1992 | Babson |
| 2008/0206751 A1 | 8/2008 | Squirrell |
| 2015/0226759 A1* | 8/2015 | Connolly ............. G01N 35/109 435/287.3 |

FOREIGN PATENT DOCUMENTS

| CN | 101147070 | 8/2006 |
| EP | 2439537 | 12/2010 |

(Continued)

OTHER PUBLICATIONS

Office Action dated Apr. 16, 2018 for CN 201710224145.3 (10 pages).

(Continued)

*Primary Examiner* — Kathryn Wright
(74) *Attorney, Agent, or Firm* — Conley Rose, P.C.

(57) ABSTRACT

A modular automatic analyzer using a circular type cartridge enabling centrifugation according to an exemplary embodiment of the present invention includes: a main body frame; an X-axis conveying unit which reciprocally moves in an X-axis direction with respect to the main body frame; a circular type cartridge accommodating housing which is installed with respect to the X-axis conveying unit so as to be reciprocally movable in the X-axis direction by the X-axis conveying unit, a single rotation drive unit which is installed in the circular type cartridge accommodating housing and is rotated step by step at a predetermined interval or rotated at a high speed for centrifugation, a circular type cartridge which is installed at an upper surface of the circular type cartridge accommodating housing so as to be rotatably connected to the rotation drive unit and has wells disposed to be spaced apart from each other at predetermined intervals in a circumferential direction of a disc-shaped main body, a tip lifting unit which picks up and moves a tip upward and downward, a measurement unit which measures a reaction in the well, a Z-axis drive unit which is provided (Continued)

with the tip lifting unit and the measurement unit and reciprocally operates in a Z-axis direction with respect to the main body frame, and a control unit C which controls an automatic immunity analyzer.

12 Claims, 7 Drawing Sheets

(51) Int. Cl.
  *B04B 15/02*   (2006.01)
  *B04B 5/04*    (2006.01)
  *B04B 7/02*    (2006.01)
  *G01N 35/00*   (2006.01)
  *B01L 3/00*    (2006.01)
  *G01N 21/07*   (2006.01)
  *G01N 33/49*   (2006.01)
  *G01N 21/76*   (2006.01)

(52) U.S. Cl.
  CPC ............... *B04B 7/02* (2013.01); *B04B 15/02* (2013.01); *G01N 21/07* (2013.01); *G01N 33/491* (2013.01); *G01N 35/00* (2013.01); *G01N 35/00623* (2013.01); *G01N 35/04* (2013.01); *G01N 21/76* (2013.01); *G01N 2035/00306* (2013.01); *G01N 2035/00376* (2013.01); *G01N 2035/00495* (2013.01); *G01N 2035/00504* (2013.01); *G01N 2035/0439* (2013.01); *G01N 2035/0449* (2013.01)

(56) References Cited

FOREIGN PATENT DOCUMENTS

| | | |
|---|---|---|
| EP | 2835178 | 8/2013 |
| JP | 6113162 | 1/1986 |
| JP | 09033535 | 2/1997 |
| JP | 2731626 | 3/1998 |
| JP | 2008-76256 | 4/2008 |
| JP | 2011501132 | 1/2011 |
| WO | WO2005/057224 | 6/2005 |
| WO | 2009093731 | 7/2009 |
| WO | WO2010/140680 | 12/2010 |
| WO | WO2014/014016 | 1/2014 |

OTHER PUBLICATIONS

Office Action dated Feb. 2, 1018 for JP 2017-076610 (4 pages).
English abstract of JP2008076256A (1 page).
English abstract of JP09-33535 (1 page).
JP273162B English Translation of Abstract.
JP2011501132 English Translation of Abstract.
JPS6113162 English Translation of Abstract.
European Search Report for EP Application 17165337.1 dated Aug. 21, 2017 (10 Pages).
Office Action dated Aug. 30, 2017 in Korean Patent Application No. 10-2016-0043177.

* cited by examiner (a)  (b)

CIRCULAR TYPE CARTRIDGE ENABLING CENTRIFUGATION AND MODULAR AUTOMATIC ANALYZER USING THE SAME

CROSS-REFERENCE TO RELATED APPLICATION

This application claims priority to and the benefit of Korean Patent Application No. 10-2016-0043177 and 10-2017-0035572 filed in the Korean Intellectual Property Office on Apr. 8, 2016 and Mar. 21, 2017, the entire contents of which are incorporated herein by reference.

BACKGROUND OF THE INVENTION (a) Field of the Invention

The present invention relates to a circular type cartridge enabling centrifugation and a modular automatic analyzer using the same, and more particularly, to a circular type cartridge enabling centrifugation, in which red blood cells and plasma separated from whole blood by using the circular type cartridge are used, and as a result, a separate input by an inspector is not required, measurement accuracy may be improved, design becomes compact and optimized such that a plurality of modular automatic analyzers may be combined and expanded in a modular manner, and diagnosis of various items or various diseases may be performed for a minimum period of time, and a modular automatic analyzer using the same.

(b) Description of the Related Art

An automatic analyzer in the related art, which measures components in biological samples such as blood samples or urine samples, mainly measures biochemical items such as enzymes. However, recently, the automatic analyzer increasingly measures immunological items such as hormones or tumor markers. In general, a biochemical automatic analyzer measures test substances by means of transmitted light or scattered light by using a change in light absorbance of a reaction liquid caused by a biochemical reaction in blood samples.

Meanwhile, a seroimmunity analyzer for immunological items measures a test substance such as hormones in biological substances with high sensitivity by immunologically reacting and binding a labelled antibody or a labelled antigen, in which an antibody or an antigen, which specifically binds to each test substance prepared as a reagent and, with a fluorescent dye or the like, to the test substance in the sample, performing B/F separation, and heterogeneously detecting the labelled antibody or the labelled antigen.

Here, the B/F separation means that binding components (bind B), which are subjected to the analysis, and free components (free F), which are not subjected to the analysis, are separated.

Recently, the necessity of measuring the same specimen for a plurality of immunological items as well as the biochemical items is increased.

For example, in some instances, it is necessary to simultaneously diagnose cancer and cardiac diseases, or it is necessary to simultaneously measure both of the biochemical item and the immunological item for the purpose of accuracy when testing a thyroid gland function.

However, in the case of the automatic analyzer in the related art, it is necessary to complete the measurement by using the seroimmunity analyzer with a linear cartridge structure and then measure the specimen again by using the biochemical automatic analyzer, or it is necessary to complete the measurement by using the biochemical automatic analyzer and then measure the specimen again by using the seroimmunity analyzer.

In addition, in most instances, a test result obtained by a single automatic analyzer is insufficient to obtain a precise result.

In particular, presently, immunity equipment for diagnosing cardiovascular vessels has a function of simultaneously diagnosing six channels, but there is a drawback in that the equipment cannot be used during the test, and it is necessary to individually and simultaneously perform the tests when emergency patients are simultaneously hospitalized. Therefore, multi-channel analysis functions, which may be individually operated, are required for the automatic analyzer used under an emergency environment.

However, in this case, in a case in which multiple automatic analyzers are used in the related art, there is a problem in that an overall size is too large.

In addition, the immunity measurement equipment measures a particular biomarker protein concentration in human plasma or serum, and in this case, it is not necessary to correct measured concentration when the plasma or the serum is directly used as a measurement sample, but it is necessary to correct a measured concentration by using a volume ratio of red blood cells in the sample when whole blood is used.

Therefore, in the case of most existing equipment, a volume ratio of red blood cells, which is separately measured at the outside, and a type of sample (whole blood/plasma/serum) needs to be inputted to the equipment.

That is, in the case of most of the automatic analyzers the related art, it is necessary to use the red blood cells and the plasma which are separated from the whole blood in advance, or it is necessary to input a numerical value of red blood cells of a subject into the automatic analyzer, and as a result, there is a problem in that inconvenience is caused and test accuracy deteriorates in some instances.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a circular type cartridge enabling centrifugation, in which red blood cells and plasma separated from whole blood by using the circular type cartridge in an automatic analyzer are used, and as a result, a separate input by an inspector is not required, measurement accuracy may be improved, design becomes compact and optimized such that an overall size of a system may be reduced even though a plurality of modular automatic analyzers is combined and expanded in a modular manner, and diagnosis of various items or various diseases may be performed for a minimum period of time, and a modular automatic analyzer using the same.

An exemplary embodiment of the present invention provides a modular automatic analyzer using a circular type cartridge enabling centrifugation, the modular automatic analyzer including: a main body frame; an X-axis conveying unit which reciprocally moves in an X-axis direction with respect to the main body frame; a circular type cartridge accommodating housing which is installed with respect to the X-axis conveying unit so as to be reciprocally movable in the X-axis direction by the X-axis conveying unit, a single rotation drive unit which is installed in the circular type cartridge accommodating housing and is rotated step by step at a predetermined interval or rotated at a high speed for centrifugation, a circular type cartridge which is installed at an upper surface of the circular type cartridge accommodating housing so as to be rotatably connected to the rotation drive unit and has wells disposed to be spaced apart from each other at predetermined intervals in a circumferential direction of a disc-shaped main body, a tip lifting unit which picks up and moves a tip upward and downward, a measurement unit which measures a reaction in the well, a Z-axis drive unit which is provided with the tip lifting unit and the measurement unit and reciprocally operates in a Z-axis direction with respect to the main body frame, and a control unit C which controls an automatic immunity analyzer.

Another exemplary embodiment of the present invention provides a circular type cartridge enabling centrifugation, which is installed at an upper side of a circular type cartridge accommodating housing, and has a centrifugation well for centrifugation of a sample, and two or more wells for testing the sample with a rotation type.

According to an exemplary embodiment of the present invention, there may be provided the modular automatic analyzer having the circular type cartridge, in which the red blood cells and the plasma separated from the whole blood by using the circular type cartridge in the automatic analyzer are used, and as a result, a separate input by an inspector is not required, measurement accuracy may be improved, design becomes compact and optimized such that an overall size of a system may be reduced even though a plurality of modular automatic analyzers is combined and expanded in a modular manner, and diagnosis of various items or various diseases may be performed for a minimum period of time.

DETAILED DESCRIPTION OF THE EMBODIMENTS

Figure 1:
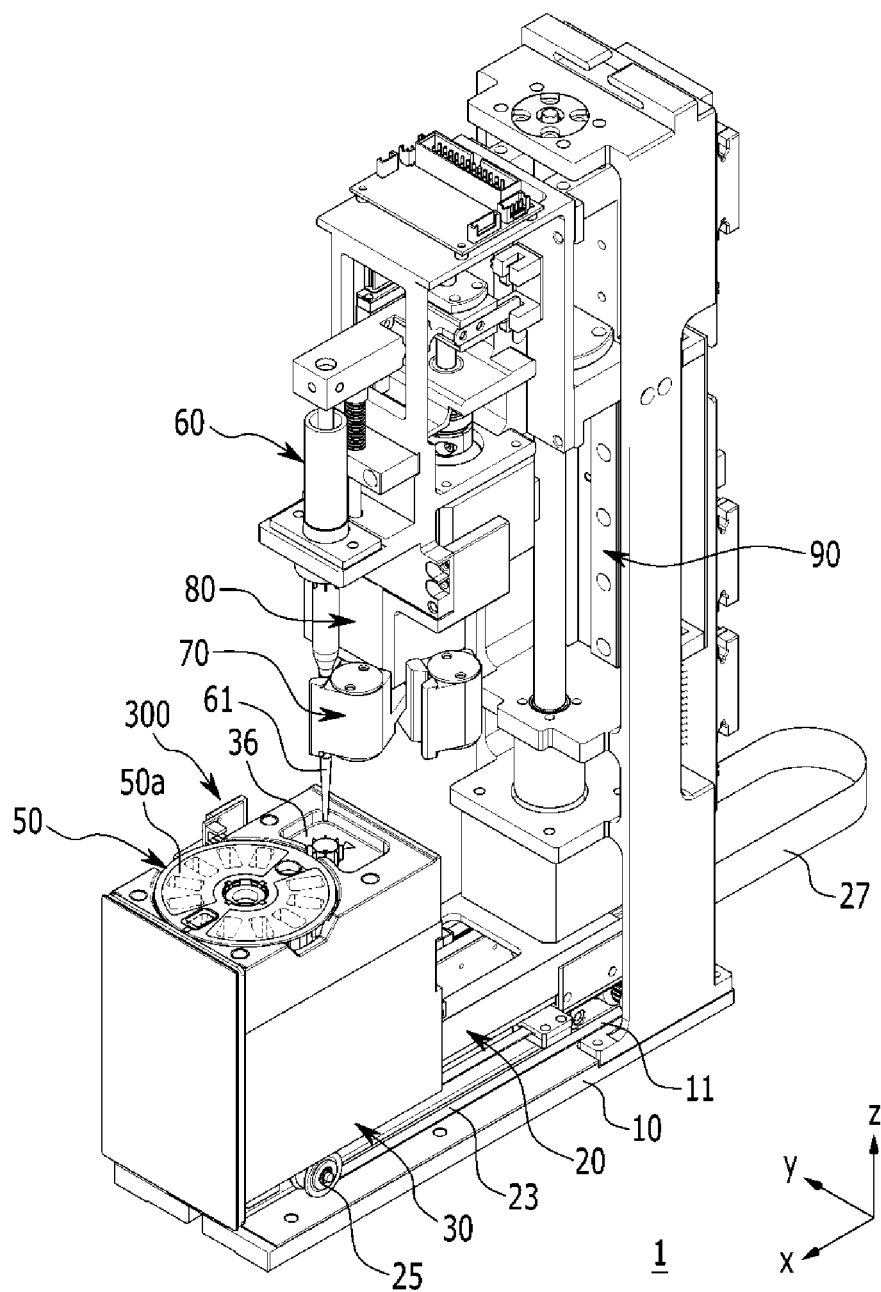
FIG. 1 is a perspective view of a modular automatic analyzer having a circular type cartridge according to an exemplary embodiment of the present invention.

In the following detailed description, only certain example embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

Throughout the specification, unless explicitly described to the contrary, the word "comprise" and variations such as "comprises" or "comprising" will be understood to imply the inclusion of stated elements but not the exclusion of any other elements. In addition, the terms "-er", "-or" and "module" described in the specification mean units for processing at least one function and operation and can be implemented by hardware components or software components and combinations thereof.

Hereinafter, a modular automatic analyzer having a circular type cartridge according to an exemplary embodiment of the present invention will be described in detail with reference to the accompanying drawings.

Figure 2:
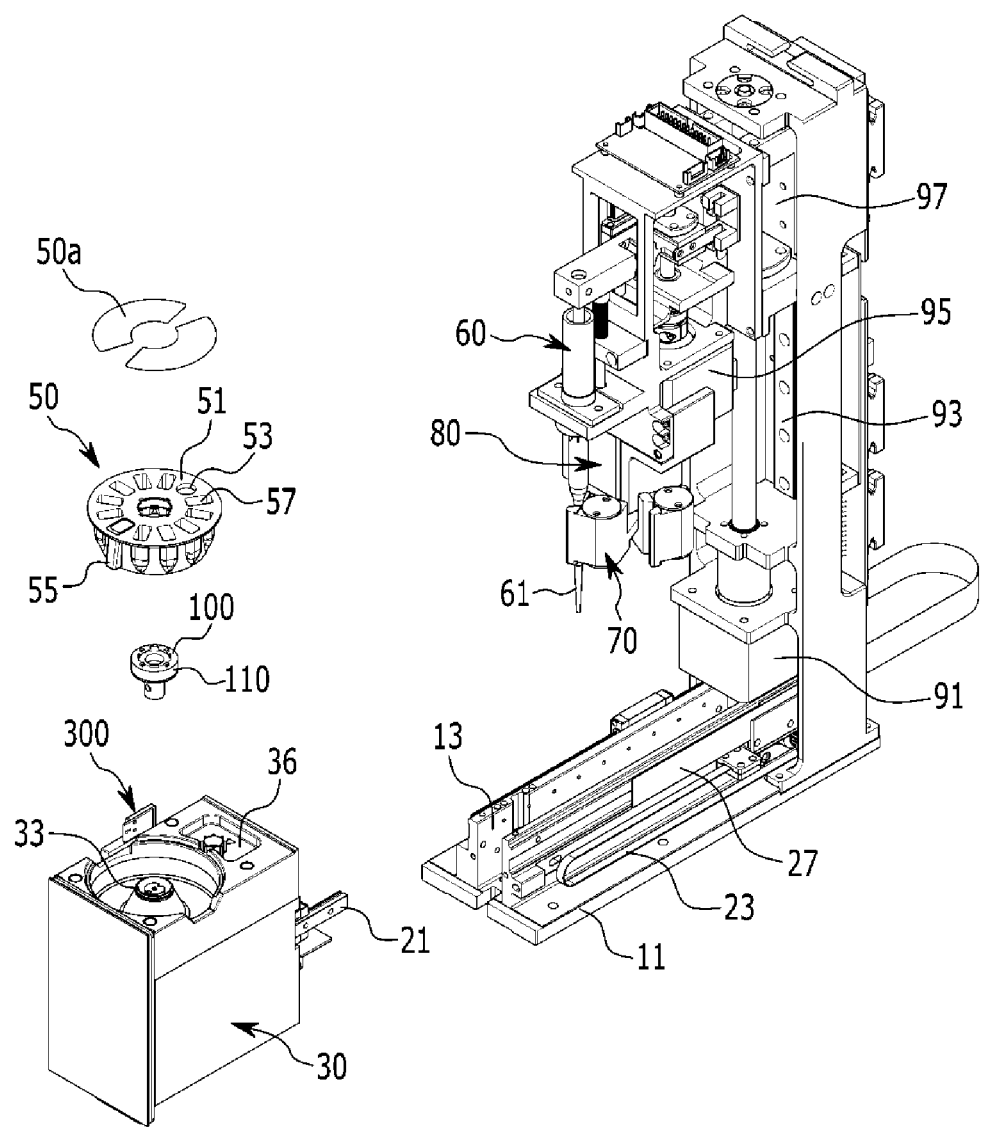
FIG. 2 is an exploded perspective view of FIG. 1 for explaining a reciprocal operation in an X-axis direction of a circular type cartridge accommodating housing and a change of circular type cartridges.
Figure 3:
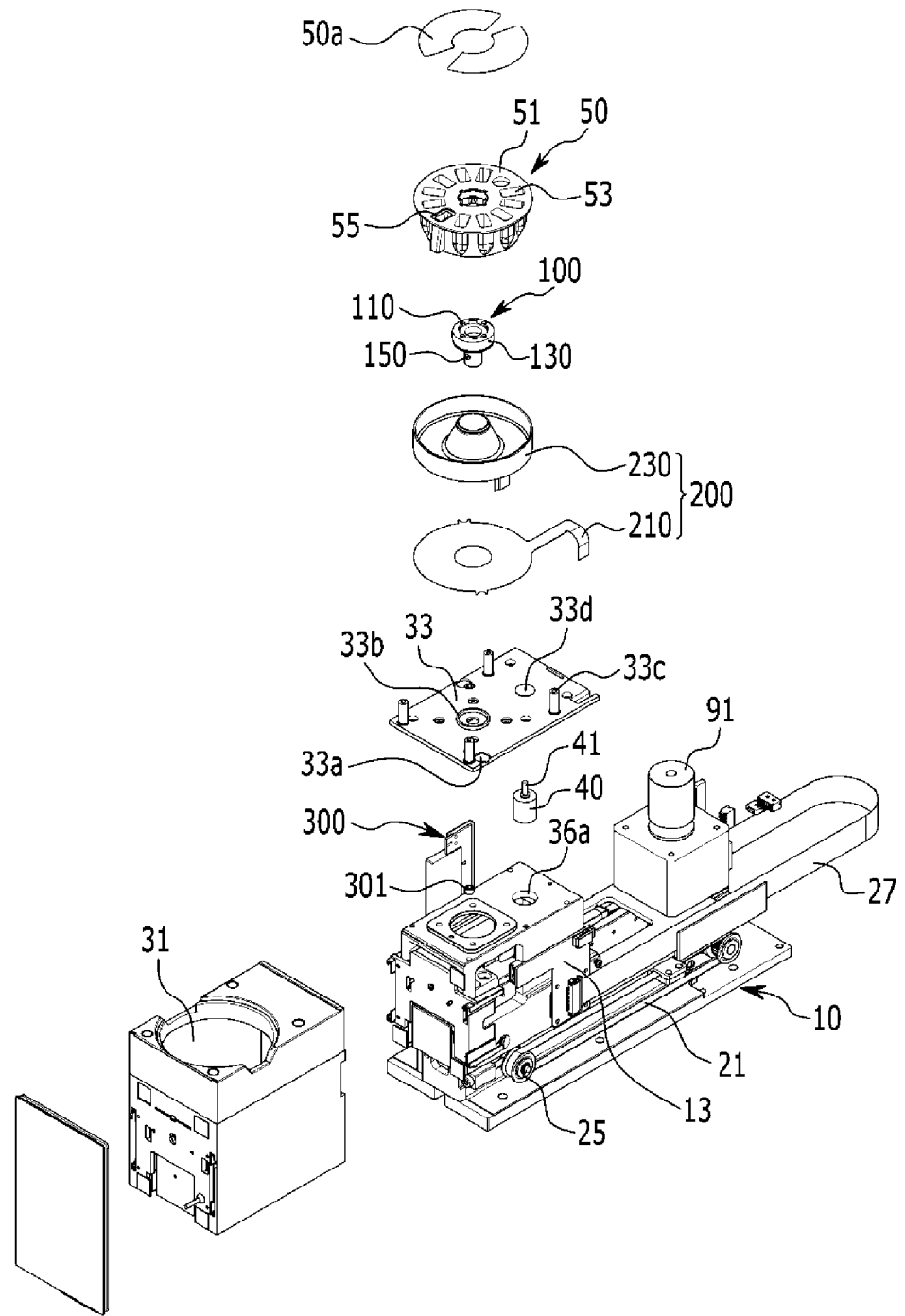
FIG. 3 is an exploded perspective view of part B in FIG. 2 for explaining a configuration of the circular type cartridge accommodating housing.

As illustrated in FIGS. 1 to 3, a modular automatic analyzer 1 having a circular type cartridge according to an exemplary embodiment of the present invention includes a plate-shaped main body frame 10 which is disposed at a bottom side of an exterior housing 1a, an X-axis conveying unit 20 which reciprocally moves in an X-axis direction with respect to the main body frame 10, a circular type cartridge accommodating housing 30 which is installed to the X-axis conveying unit 20 so as to be reciprocally movable in the X-axis direction by the X-axis conveying unit 20, a rotation drive unit 40 which is installed in the circular type cartridge accommodating housing 30, a circular type cartridge 50 which is installed at an upper side of the circular type cartridge accommodating housing 30 so as to be rotatably connected to the rotation drive unit 40, and has two or more wells 53 disposed to be spaced apart from each other at predetermined intervals in a circumferential direction of a disc-shaped main body 51, a tip lifting unit 60 which picks up and moves a tip 61, which is used for performing an analysis process such as processes of injecting, mixing, and cleaning a sample, upward and downward with respect to the two or more wells 53, a measurement unit 70 which measures reactions in the two or more wells 53, a magnetron 80 which generates microwaves to form the reactions in the two or more wells 53, a Z-axis drive unit 90 which is provided with the tip lifting unit 60 and the measurement unit 70 and reciprocally operates the tip lifting unit 60 and the measurement unit 70 in a Z-axis direction with respect to the main body frame 10, and a control unit C which controls the respective constituent elements of the automatic immunity analyzer 1.

In the automatic immunity analyzer 1 having the aforementioned structure, the main body frame 10 has L-shaped opened structures each of which includes a stationary guide rail 23 of the X-axis drive unit 20 to which an X-axis moving rail 21 mounted at a lower side of the circular type cartridge accommodating housing 30 is movably coupled, a base portion 11 which extends in the X-axis direction and has an auxiliary roller 25 for assisting the movement of the X-axis moving rail 21, and a sidewall portion 13 which extends in the Z-axis direction with respect to the base portion 11.

In the X-axis drive unit 20 as described above, the X-axis moving rail 21 may freely move in the X-axis direction along the stationary guide rail 23 with respect to the base portion 11 of the main body frame 10, and as a result, it is easy to mount and change the circular type cartridge 50 and to repair other equipment by withdrawing the circular type cartridge accommodating housing 30.

The circular type cartridge accommodating housing 30 has a hollow shape having a vacant interior, and may include the circular type cartridge 50, a fan unit 100 which rotates the circular type cartridge 50 at a predetermined rotational speed and generates forced convection at a lower side of the circular type cartridge 50 while simultaneously rotating, an accommodating chamber 31 which is installed around the fan unit 100 and accommodates a heater unit 200 for supplying predetermined heat so that the well 53 at the lower side of the circular type cartridge 50 comes into the atmosphere at a predetermined temperature, and a partition wall portion 33 which is installed in the circular type cartridge accommodating housing 30 so that the accommodating chamber 31 may serve as a predetermined chamber.

The circular type cartridge housing 30 may include a tip mounting portion 36 which is used to attach and detach the tip 61 independently of the circular type cartridge accommodating chamber 31.

The tip mounting portion 36 further includes a tip accommodating hole 36*a* having a shape corresponding to the tip so as to accommodate and protect the tip 61, and the tip accommodating hole 36*a* is disposed to be adjacent to the accommodating chamber 31 so that the tip 61 is easily moved to a test position of the circular type cartridge 50.

Meanwhile, whether the circular type cartridge housing 30 is positioned at a test position of the tip 61 where a sample test is performed or an attaching and detaching position of the tip 61 before the sample test starts or after the sample test ends may be automatically detected by a position sensor 300 installed along a sidewall of the circular type cartridge housing 30.

Therefore, it is possible to assuredly detect points in time at which the sample test process starts and ends, and thus it is possible to prevent the measurement unit 70 or the magnetron 80 from operating when the tip 61 is positioned at the attaching and detaching position of the tip 61.

The partition wall portion 33 may be provided with an electric power line connecting hole 33*a* through which an electric power line for supplying electric power to the heater unit 200 passes, a through hole 33*b* which is penetrated by a rotating shaft 41 of the rotation drive unit 40, a mounting hole 33*c* in which a fixing means (not illustrated) for fixing the rotation drive unit 40 is installed, and a communication hole 33*d* which communicates with the tip accommodating hole 36*a*.

The fan unit 100 may include a disc-shaped circular type cartridge support portion 110 which has a coupling protrusion 110*a* coupled to a coupling groove 51*a* in a central hole of the circular type cartridge 50 so as to support the circular type cartridge 50 such that the circular type cartridge 50 is changeable and rotatable, a blade portion 130 which extends from the circular type cartridge support portion 110, and a cartridge holder 150 which is coupled to a center of the circular type cartridge support portion 110 and connected to the rotating shaft 41 of the rotation drive unit 40 so as to transmit rotational force of the rotation drive unit 40 to the circular type cartridge 50 and the blade portion 130.

A plurality of blade portions 130 may be mounted at a lower side of the circular type cartridge support portion 110 so as to be spaced apart from each other at predetermined intervals, or the blade portion 130 may be mounted in the form of a single flange.

The rotation drive unit 40 may include the rotating shaft 41, and a single motor 43 which is coupled to the rotating shaft 41 and rotates step by step so that each of the wells 53 of the circular type cartridge 50 may be disposed at a lower side of the tip 61 by being controlled by the control unit C, or rotates at a high speed so that the sample in the well 53 may be centrifuged.

A step motor, a spindle motor, a BLDC motor, and the like may be used as the motor 43 so that the motor may rotate step by step and at a high speed simultaneously.

The heater unit 200 may be a heater coil which generates heat when electric power is applied to the heater coil.

The heater unit 200 includes a heating block 210 which is made of a heat radiating metallic material having a container shape for accommodating the two or more wells at the lower side of the circular cartridge 50, and a plate-shaped thermistor 230 which is installed at a bottom of the heating block 210, and the heater unit 200 is installed to be spaced apart at a predetermined interval from a bottom of the hollow chamber 31, and may be thermally insulated from the periphery.

The heating block 210 is made of aluminum having excellent heat radiating properties and coupled to the fan unit 100 so as to quickly heat an interior of the accommodating chamber 31 to a temperature for the test, and the interior of the accommodating chamber 31 may be cooled to an original temperature after the test ends.

When heat is transmitted to the heater unit 200, the blade portion 130, which extends from the circular type cartridge support portion 110 with respect to an internal space of the accommodating chamber 31, generates forced convection of inside air by the rotation of the motor 43, thereby quickly and uniformly adjusting a temperature similar to the interior of the chamber.

Now, the circular type cartridge according to an exemplary embodiment of the present invention will be described in detail with reference to FIG. 4.

Figure 4:
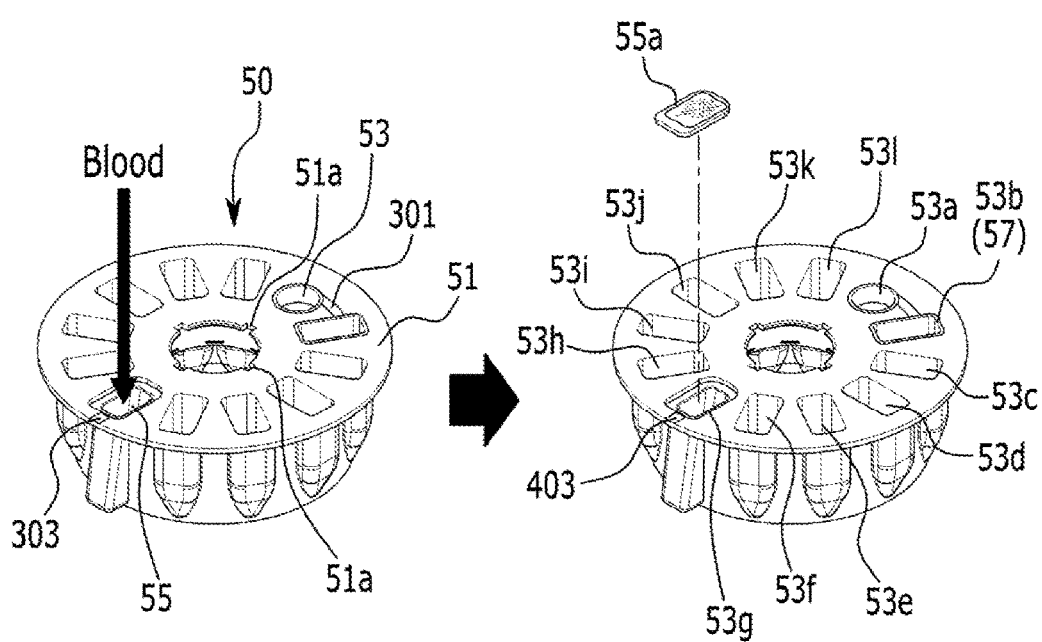
FIG. 4 is a conceptual perspective view for explaining a configuration of and a method of using the circular type cartridge according to an exemplary embodiment of the present invention.

FIG. 4 is a conceptual perspective view for explaining a configuration of and a method of using the circular type cartridge according to an exemplary embodiment of the present invention.

As illustrated in FIG. 4, the circular type cartridge 50 according to an exemplary embodiment of the present invention may have at least a pair of coupling grooves 51*ab* at the opposite positions in a central hole 51*a* of the disc-shaped main body 51 so as to be fitted with the fan unit 100.

The coupling grooves 51*ab* not only serve as a positioning unit for determining positions of the two or more wells 53, but also have an original point indicating unit 303 provided at an outer side in a radial direction of the two or more wells 53 so as to indicate a start point of an automatic analysis process by the movement of the two or more wells 53.

Therefore, the well, which is adjacent to the original point indicating unit 303, is used as a centrifugation well 55, and the well 53, which is positioned farthest away from the centrifugation well 55, is used as a detection well, and the well, which is adjacent to the detection well, is specified as a magnetic particle well 57 that accommodates magnetic particles.

That is, an original point may be simply sensed by using the original point indicating unit 303 and the coupling groove 51*ab* when the circular type cartridge 50 is mounted in the circular type cartridge accommodating chamber 31.

The other two or more wells 53 may be covered by a film type cover portion 50*a* in order to prevent contamination, and the well 55 for centrifugation accommodates a sample such as blood and may be separately provided with a cap 55*a* that covers an opening portion of the well 55 in order to prevent the sample from leaking to the outside during the centrifugation.

The cap 55*a* prevents a leak of the sample such as blood during the centrifugation, and may be formed in the form of a (thin) film which may be penetrated by the tip 61 by the movement of the tip lifting unit 60 so that the tip 61 may approach the well so as to separate plasma and serum after the centrifugation, and a rim is formed at a circumference of the cap 55*a* so as to tautly hold a central portion of the cap 55*a*, if possible, such that a position of the cap may be maintained even though the tip 61 penetrates the cap 55*a*.

The position sensor 300, which obtains information about the positions of the respective wells 53 and recognizes the positions of the respective wells 53 in order to allow a reagent to react at the positions of the respective wells 53 of the circular type cartridge 50, may be disposed to protrude in the Z-axis direction from a particular position with respect to a side of the circular type cartridge accommodating housing 30.

In addition, position indicating units 301, which indicate information about the positions of the respective wells 53 may be further included in the respective wells 53 of the circular type cartridge 50 so as to correspond to the position sensor 300.

One of the position indicating units 301 may be elongated in a Y-axis direction at an end of an upper surface of the circular type cartridge accommodating housing 30, and may indicate the test position of the tip 61 and the attaching and detaching position of the tip 61 which will be described below in detail.

The control unit C may control the rotation drive unit 40 in conjunction with the position sensor 300 which reads position indicating units 303 indicated on the respective cells 53 of the circular type cartridge 50 when the rotation drive unit 40 rotates step by step so that the rotation drive unit 40 may rotate exactly to the respective cells 53.

The well 53 accommodates a whole blood sample, and the centrifugation well 55 for performing the centrifugation may be configured to be inclined at a predetermined angle in a centrifugation direction so as to separate plasma and blood cells while preventing the whole blood sample from contaminating other wells or devices due to the centrifugation.

The tip 61 may be detachably coupled to the tip lifting unit 60 by various methods, and may be controlled so that the magnetic particle in the magnetic particle well 57 may be attached to and detached from the tip 61.

In the automatic analyzer according to an exemplary embodiment of the present invention, the measurement unit 70 is configured to detect a reaction by using chemiluminescence enzyme immunoassay (CLEIA), the tip 61 serves to form an immune complex by mixing antibodies labelled by a predetermined labeler and a specimen by an operation of the tip lifting unit 60, remove non-binding antibodies, and add a chemiluminescent substrate to the immune complex.

When the immune complex is incubated on the chemiluminescent substrate for a moment, light emission is detected by an enzyme reaction.

The magnetron 80 serves to generate and emit microwaves to add the chemiluminescent substrate to the immune complex, and the measurement unit 70 may include a light amplifying element that measures the light emission.

The Z-axis drive unit 90 may include a drive motor 91 which provides Z-axis driving power, a sliding unit 93 which slides the tip lifting drive unit 60 in the Z-axis direction when the drive motor 91 operates, a hydraulic pressure supply unit 95 which supplies hydraulic pressure for a pipetting operation of the tip 61 mounted on the tip lifting drive unit 60, and a Z-axis plate 97 which fixedly supports the tip lifting drive unit 60, the hydraulic pressure supply unit 95, the magnetron 80, and the measurement unit 70.

In the modular automatic analyzer 1 having the circular type cartridge according to an exemplary embodiment of the present invention, when the circular type cartridge 50 is loaded into the automatic analyzer 1 by the X-axis drive unit 20, a quick analysis may be performed within 15 seconds by the operation of the rotation drive unit 40 that rotates the circular type cartridge 50 step by step and the operation of the Z-axis drive unit 90 that operates the tip lifting unit 60 and the like.

An automatic immunity analysis method using the modular automatic analyzer 1 having the circular type cartridge according to an exemplary embodiment of the present invention will be briefly described with reference to FIG. 4 again.

In the modular automatic analyzer 1 having the circular type cartridge according to an exemplary embodiment of the present invention, various solutions may be stored in the wells 53 of the circular type cartridge 50 or the tip 61 may be put into the wells 53.

As illustrated in FIG. 4, for example, a number one well 53*a* stores a sample and allows the tip 61 to be put therein, a number two well 53*b* stores a specimen with a beads solution including magnetic particles, a number three well 53*c* has a first reagent, which binds the magnetic particles to a particular component in the sample, such that the first reagent is mixed with the specimen, a number four well 53*d* allows the specimen and an antibody to react, number five, and seven to nine wells 53*e*, and 53*g* to 53*i* store a washing liquid so as to perform the B/F separation by washing, a number six well 53*f* allows a marker substance, which emits light by an electrochemical reaction, to be labelled and stores a second reagent binding to a particular component in the sample, a number ten well 53*j* stores a buffer solution including a substance that induces electrical chemiluminescence of the marker substance, a number eleven well 53*k* accommodates a waste liquid, and a number twelve well 53*l* stores a reaction product, such that the measurement may be performed by the measurement unit 70 in accordance with a reaction program of the control unit.

As described above, the sample, the buffer solution, the washing liquid, and the various reagents are accommodated in the circular type cartridge 50, the circular type cartridge 50 is mounted in the accommodating chamber 31 of the circular type cartridge accommodating housing 30 withdrawn in the X-axis direction from the automatic analyzer 1, and the circular type cartridge accommodating housing 30 returns back to an original position, such that the circular type cartridge 50 is loaded into the automatic analyzer 1.

The number one well 53*a* is disposed at the lower side of the tip lifting unit 60 by the step-by-step rotation of the rotation drive unit 40, the tip lifting unit 60 is moved downward by the Z-axis operation of the Z-axis drive unit 90, and the tip 61 is mounted on the tip lifting unit 60.

The rotation drive unit 40 rotates at a high speed for a predetermined period of time, and the centrifugation of the whole blood accommodated in the number one well 53*a* is performed, such that the whole blood may be separated into blood cells and plasma.

Therefore, according to an exemplary embodiment of the present invention, an operator need not perform the centrifugation in advance at the outside of the automatic analyzer 1, or need not separately input a volume ratio of red blood cells for correction, whether the type of sample is whole blood or plasma, and the like.

In this case, heat is applied through the heater unit 200 by the control unit C, and air is circulated in the accommodating chamber 31 by operating the fan unit 100 connected to the rotating shaft 41 of the rotation drive unit 40, such that a predetermined temperature is quickly maintained similar to a chamber.

The tip 61 is moved downward to the number one well 53a by the tip lifting unit 60 and pipets the plasma, and then moved upward by the tip lifting unit 60, and when the number two well 53b is disposed at the lower side of the tip lifting unit 60 by the step-by-step rotation of the rotation drive unit 40, the tip lifting unit 60 is moved downward, such that the plasma, as a specimen, may be stored in the number two well 53b.

As the rotation drive unit 40 rotates step by step, the sample in the number three well 53c and the plasma in the number two well 53b may be mixed in the number three well 53c by the upward and downward operations of the tip lifting unit 60.

The immune reaction is performed in the number four well 53d by the step-by-step rotation of the rotation drive unit 40 and by microwaves emitted by the magnetron 80, and the tip 61 may be washed for the B/F separation by using the washing liquid accommodated in the number five well 53e while being moved upward and downward by the operation of the tip lifting unit 60.

A label reaction, in which the marker substance, which emits light by an electrochemical reaction, binds to a particular substance in the sample, is performed in the number six well 53f, and the test is performed in accordance with a washing step and a reaction step using the magnetic particle by protocol of the control unit C.

When the reaction produce is produced in the number twelve well 53l, the number twelve well 53l is disposed at the position of the number seven well 53g, that is, at the lower side of the measurement unit 70 by using the rotation drive unit 90, fluorescence is detected by the measurement unit 70, the tip 61 is separated from the tip lifting unit 60 and disposed in the number one well 53a, and then the circular type cartridge 50 may be unloaded.

As described above, according to the modular automatic analyzer 1 using the circular type cartridge according to an exemplary embodiment of the present invention, the centrifugation is enabled by using the circular type cartridge 50, and whole blood is separated into blood cells and plasma, such that a user may obtain an accurate result without separately inputting a volume ratio of red blood cells.

Of course, the disposition of the wells 53 may be appropriately changed in accordance with an immunity analysis environment. As described above, the immunity analysis process such as agitation and attachment is performed by storing the solutions in the respective wells 53 and then inserting the tip 61, and the operation of the tip 61 may be controlled by various methods.

Now, a door for withdrawing the circular type cartridge accommodating housing 30 installed in the exterior housing 1a of the modular automatic analyzer 1 using the circular type cartridge according to an exemplary embodiment of the present invention will be described in detail with reference to FIG. 5.

Figure 5:
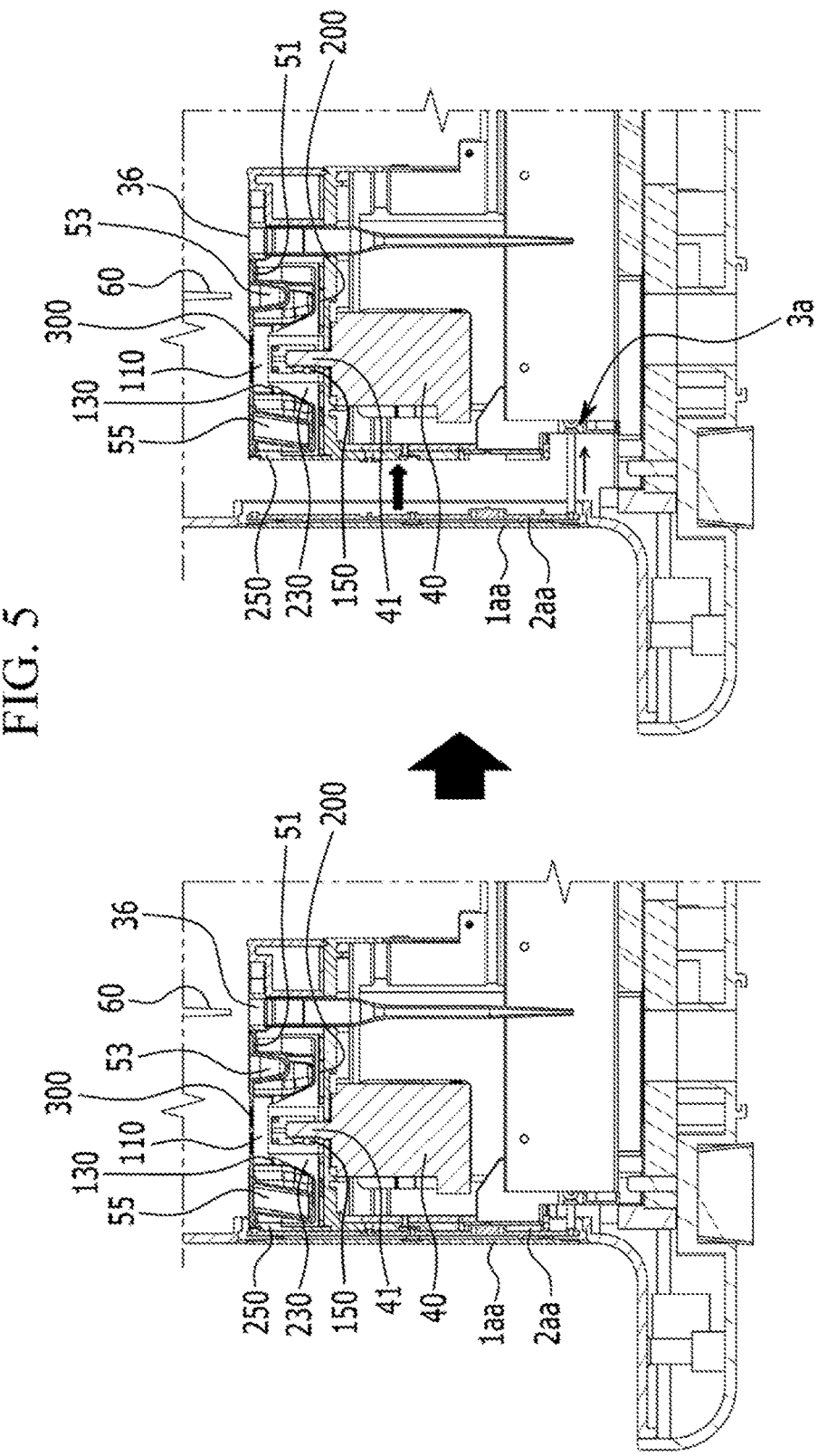
FIG. 5 is a cross-sectional view, before and after test, for explaining a dual door structure of a modular automatic analyzer using the circular type cartridge according to an exemplary embodiment of the present invention.

FIG. 5 is a cross-sectional view, before and after test, for explaining a dual door structure of the modular automatic analyzer 1 using the circular type cartridge according to an exemplary embodiment of the present invention.

Since the circular type cartridge housing 30 has the tip mounting portion 36 for attaching and detaching the tip 61 independently of the circular type cartridge accommodating chamber 31 and thus the test position is different from the attaching and detaching position of the tip, when the exterior housing 1a has a single door, the door may move forward and rearward with respect to the exterior housing 1a in accordance with the movement of the circular type cartridge housing 30.

In contrast, to solve the aforementioned problem, the modular automatic analyzer 1 using the circular type cartridge according to an exemplary embodiment of the present invention includes a first door 1aa which does not move forward and rearward with respect to the exterior housing 1a, which accommodates the circular type cartridge accommodating housing 30, so as to independently withdraw the circular type cartridge accommodating housing 30, and a second door 2aa which forms a dual structure together with the first door 1aa, such that the second door 2aa may move forward and rearward along the circular type cartridge accommodating housing 30.

In this case, the second door 2aa is connected to the circular type cartridge accommodating housing 30 by means of an elastic member 3a, elastically moves forward and rearward between the test position of the tip 61 and the attaching and detaching position of the tip 61 together with the circular type cartridge accommodating housing 30, and absorbs vibration, such that the first door 1aa of the exterior housing 1a may be held without being moved forward and rearward and without great vibration.

In addition, the position sensor 300 is attached to a side of the circular type cartridge housing 30 and checks the test position of the tip in conjunction with the position indicating unit 301 for indicating the test position of the tip and the attaching and detaching position of the tip, and as a result, it is possible to prevent malfunctions of other equipment.

Now, an expanded form of the modular automatic analyzer having the circular type cartridge according to an exemplary embodiment of the present invention will be described with reference to FIGS. 6 and 7.

Figure 6:
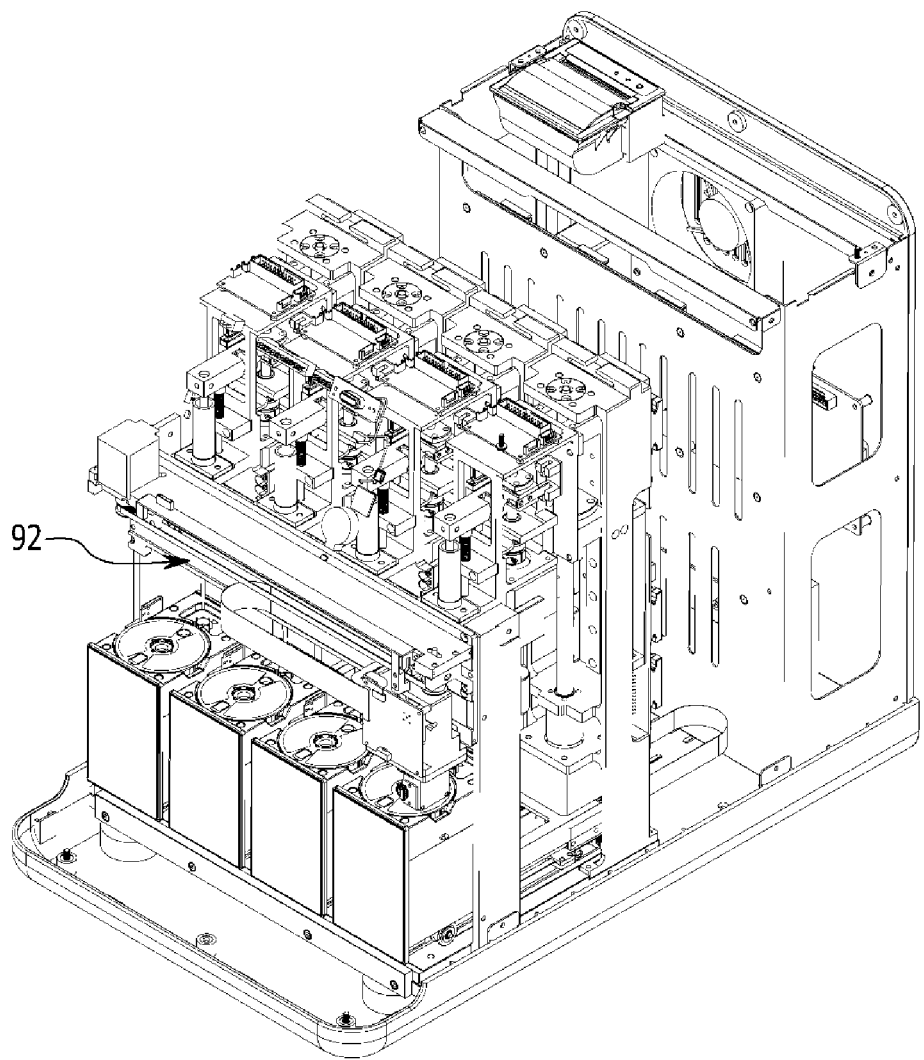
FIG. 6 is an exploded perspective view illustrating an expanded form of the modular automatic analyzer having the circular type cartridge according to an exemplary embodiment of the present invention.
Figure 7:
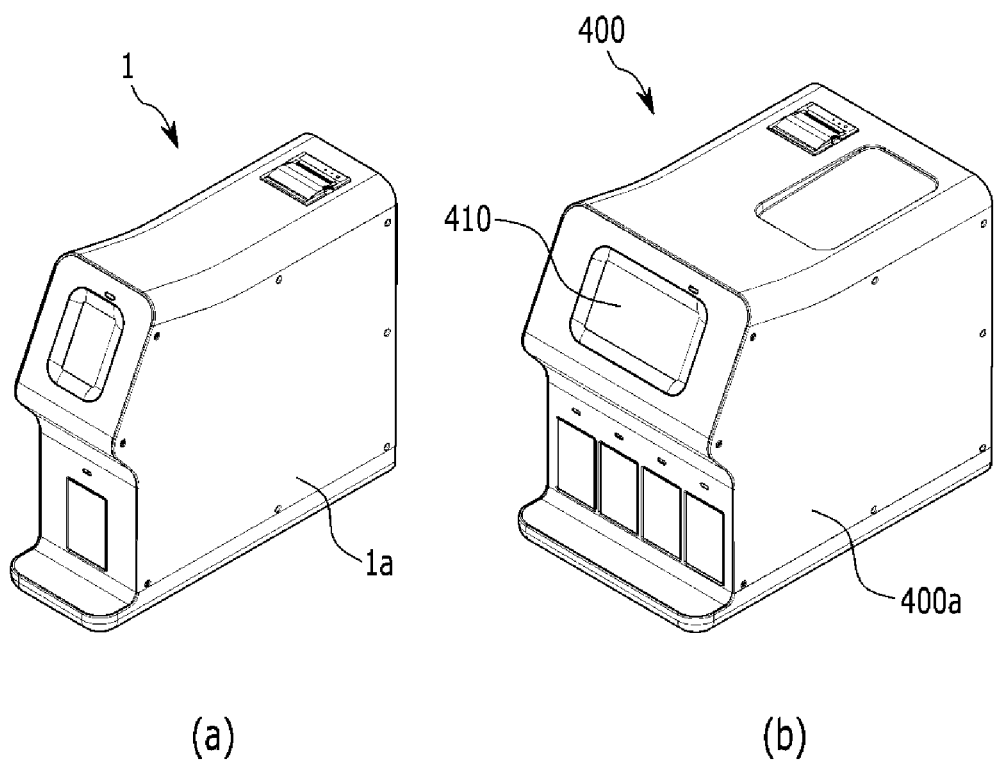
FIG. 7 is a perspective view illustrating a basic form and an expanded form of the modular automatic analyzer having the circular type cartridge according to an exemplary embodiment of the present invention.

FIG. 6 is an exploded perspective view illustrating an expanded form of the modular automatic analyzer having the circular type cartridge according to an exemplary embodiment of the present invention, and FIG. 7 is a perspective view illustrating a basic form and an expanded form of the modular automatic analyzer having the circular type cartridge according to an exemplary embodiment of the present invention.

As illustrated in FIG. 6, in the modular automatic analyzer 1 having the circular type cartridge according to an exemplary embodiment of the present invention, two or more circular type cartridge accommodating housings 30 are installed in the Y-axis direction in a single one exterior housing 1a, and may be configured to be operable independently of the single exterior housing 1a.

Of course, the tip 61, the tip lifting drive unit 60, the measurement unit 70, and the magnetron 80 may be configured to correspond to the circular type cartridge accommodating housing 30 in a one-to-one manner.

In addition, to share the tip lifting unit 60 and the measurement unit 70 with the adjacent circular type cartridge accommodating housing 30 when the centrifugation is performed in the circular cartridge 50 in the single exterior housing 1a, a belt type Y-axis direction conveying unit 92 may be added to use the tip lifting unit 60 and the measurement unit 70 by moving the tip lifting unit 60 and the measurement unit 70 in the Y-axis direction.

At least one of the Z-axis drive unit, the measurement unit, and the tip lifting drive unit may be coupled to the Y-axis direction conveying unit 92, which may be moved in the Y-axis direction, in order to share at least one of the Z-axis drive unit, the measurement unit, and the tip lifting drive unit with the circular type cartridge accommodating housings in the single exterior housing.

As illustrated in FIG. 7, in the modular automatic analyzer 1 having the circular type cartridge according to an exemplary embodiment of the present invention, a single circular type cartridge accommodating housing 30 in the exterior housing 1a having an input unit 410 may be used to be withdrawable, two or more circular type cartridge accommodating housings 30 may be installed to be usable independently of a single exterior housing 400a, the equipment mounted on the Z-axis drive unit 90 such as the measurement unit 70, the tip lifting unit 70, and the magnetron 80 may be installed to be shared, and a plurality of exterior housings each having two or more circular type cartridge accommodating housings 30 may be installed to be adjacent to each other.

The modular automatic analyzer 1 having the circular type cartridge according to an exemplary embodiment of the present invention may be easily expanded due to the modular design thereof, and thus may cope with various market situations, and may be easily subjected to maintenance.

The modular automatic analyzer 1 having the circular type cartridge according to an exemplary embodiment of the present invention independently operates, and thus may be effective in emergency treatment when a plurality of modular automatic analyzers is installed.

The modular automatic analyzer 1 having the circular type cartridge according to an exemplary embodiment of the present invention may be effective in an emergency situation because the analysis time is within 15 minutes, and may improve measurement precision by improving an analysis correlation between whole blood and blood cells because the centrifugation may be performed in the respective automatic analyzers 1.

The modular automatic analyzer 1 having the circular type cartridge according to an exemplary embodiment of the present invention may improve spatial utilization because of a compact size since the circular type cartridge 50 is used.

DESCRIPTION OF SYMBOLS

| | |
|---|---|
| 10: Main body frame | 20: X-axis drive unit |
| 30: Circular type cartridge accommodating housing | |
| 40: Rotation drive unit | |
| 50: Circular type cartridge | 60: Tip lifting drive unit |
| 70: Measurement unit | 80: Magnetron |
| 90: Z-axis drive unit | |

What is claimed is:

1. An automatic analyzer using a circular type cartridge enabling centrifugation, the automatic analyzer comprising:
   a main body frame;
   an X-axis conveying unit which reciprocally moves in an X-axis direction of forward and backward with respect to the main body frame;
   a circular type cartridge accommodating housing which is installed with respect to the X-axis conveying unit so as to be reciprocally movable in the X-axis direction by the X-axis conveying unit;
   a circular type cartridge which is installed at an upper side of the circular type cartridge accommodating housing, and has a centrifugation well for centrifugation of a sample, and two or more wells for testing the sample;
   a single rotation drive unit which selectively rotates the circular type cartridge step by step by a predetermined interval and at a high speed for centrifugation, and is installed in the circular type cartridge accommodating housing;
   a pipette tip;
   a tip lifting unit configured to move the pipette tip upward and downward for testing the well;
   a measurement unit which measures a reaction in the well;
   a Z-axis drive unit which is provided with the tip lifting unit and the measurement unit, and reciprocally operates in a Z-axis direction with respect to the main body frame, wherein the Z-axis direction is arranged transverse to the X-axis direction;
   a control unit which controls the X-axis conveying unit, the rotation drive unit, the tip lifting unit, the measurement unit, and the Z-axis drive unit so as to enable an automatic immunity analysis;
   wherein the circular type cartridge accommodating housing further includes:
      a hollow chamber which has a vacant interior so as to accommodate the circular type cartridge at the upper side thereof;
      a fan unit having a circular type cartridge support portion configured to support the circular type cartridge such that the circular type cartridge is rotatable, and a blade portion which extends from the circular type cartridge support portion, wherein the fan unit is positioned in the hollow chamber, coupled to a central hole of the circular type cartridge by being fitted into the central hole, and is configured to generate forced convection at a lower side of the circular type cartridge; and
      a heater unit which is installed around the fan unit and configured to supply a predetermined heat so that the well at the lower side of the circular type cartridge comes into an atmosphere at a predetermined temperature,
   wherein the rotation drive unit is configured to simultaneously operate the circular type cartridge and the fan unit.

2. The automatic analyzer of claim 1, wherein:
   at least a pair of coupling grooves is formed at opposite positions in the central hole of the circular type cartridge so as to engage with the fan unit, and an original point indicating unit is provided at an outer side of the circular type cartridge in a radial direction of the coupling grooves so as to indicate a start point of an automatic analysis process by a movement of the two or more wells.

3. The automatic analyzer of claim 1, wherein:
   the heater unit includes a heating block which is made of a heat radiating metallic material having a shape for accommodating the well at the lower side of the circular cartridge, and a plate-shaped thermistor which is installed adjacent to the heating block, and the heater unit is installed to be spaced apart at a predetermined interval from a bottom of the hollow chamber.

4. The automatic analyzer of claim 1, wherein:
   the circular type cartridge support portion of the fan unit is disc-shaped and includes a coupling protrusion coupled to a coupling groove in the central hole of the circular type cartridge; and the fan unit includes a cartridge holder which is coupled to a center of the circular type cartridge support portion and connected to a rotating shaft of the rotation drive unit.

5. The automatic analyzer of claim 1:
the centrifugation well is inclined radially outward in a centrifugal force direction, and includes a thin cap which covers an opening portion of the centrifugation well, such that the thin cap may be penetrated by the pipette tip in accordance with a movement of the tip lifting unit.

6. The automatic analyzer of claim 1, wherein:
a first position sensor is located on the circular type cartridge housing for sensing an original point indicating unit located on an outer side of the circular type cartridge; and
the control unit controls the rotation drive unit in conjunction with the first position sensor for selectively rotating the rotation drive unit step by step and at a high speed so that the sample is centrifuged in the centrifugation well.

7. The automatic analyzer of claim 5, wherein:
the circular type cartridge housing includes a tip mounting portion for attaching and detaching the pipette tip independently of the circular type cartridge accommodating chamber, and
the circular type cartridge housing further includes a position indicating unit for sensing a test position of the pipette tip and an attaching and detaching position of the pipette tip.

8. The automatic analyzer of claim 6, wherein:
the circular type cartridge housing further includes a position indicating unit configured to detect a test position of the pipette tip and an attaching and detaching position of the pipette tip, wherein the position indicating unit is installed on a sidewall portion of the circular type cartridge housing and protrudes in a Z-axis direction with respect to the main body frame.

9. The automatic analyzer of claim 1, further comprising:
a first door which is formed in an exterior housing of automatic analyzer in order to independently withdraw the circular type cartridge accommodating housing; and
a second door which forms a dual structure together with the first door, wherein the second door is connected to the circular type cartridge accommodating housing by means of an elastic member and moves between a test position of the pipette tip and an attaching and detaching position of the pipette tip, while the first door is fixedly held with respect to the exterior housing.

10. The automatic analyzer of claim 1, wherein:
the main body frame has L-shaped opened structures each of which includes a base portion on which the X-axis drive unit is mounted, and a sidewall portion on which the Z-axis drive unit is mounted, such that the circular type cartridge accommodating housing is configured to be withdrawn by the X-axis drive unit in the X-axis direction to the outside of the base portion.

11. The automatic analyzer of claim 1, wherein:
two or more circular type cartridge accommodating housings are installed in in a single exterior housing along a Y-axis direction transverse to the X-axis direction, and the circular type cartridge accommodating housings are operable independently of the single exterior housing.

12. The automatic analyzer of claim 11, wherein:
at least one of the Z-axis drive unit, the measurement unit, and a tip lifting drive unit is coupled to a Y-axis direction conveying unit, which is moved in the Y-axis direction, in order to share at least one of the Z-axis drive unit, the measurement unit, and the tip lifting drive unit with the circular type cartridge accommodating housings in the single exterior housing.

* * * * *